United States Patent [19]

Cooper

[11] Patent Number: 4,728,336

[45] Date of Patent: Mar. 1, 1988

[54] ALIGNMENT DEVICE FOR ARTIFICIAL LIMBS

[75] Inventor: John E. Cooper, Leatherhead, England

[73] Assignee: J. E. Hanger & Company Limited, London, England

[21] Appl. No.: 933,176

[22] Filed: Nov. 21, 1986

[30] Foreign Application Priority Data

Nov. 25, 1985 [GB] United Kingdom ............... 8528992

[51] Int. Cl.⁴ ............................................. A61F 2/80
[52] U.S. Cl. ....................................... 623/38; 623/47; 623/53
[58] Field of Search ............... 403/127, 90, 337, 143; 623/47, 48, 53, 33, 38

[56] References Cited

U.S. PATENT DOCUMENTS

| | | | |
|---|---|---|---|
| 3,273,168 | 9/1960 | Gardner | 33/180 R |
| 3,414,908 | 12/1968 | Waggott | 623/38 |
| 3,671,978 | 6/1972 | May | 623/38 |
| 3,982,278 | 9/1976 | May | 623/38 |
| 4,186,449 | 2/1980 | Horvath | 623/47 |
| 4,536,898 | 8/1985 | Palfray | 623/33 |
| 4,568,121 | 2/1986 | Hashima | 403/90 |
| 4,676,800 | 6/1987 | Chen | 623/38 |

FOREIGN PATENT DOCUMENTS 054391 6/1982 European Pat. Off. .
1307919 2/1973 United Kingdom .

Primary Examiner—Richard J. Apley
Assistant Examiner—James Prizant
Attorney, Agent, or Firm—Shoemaker and Mattare, Ltd.

[57] ABSTRACT

A first member of an artificial limb such as a tube socket has a generally rhombic flange formed with through-holes grouped into an anterior-posterior pair and a medial/lateral pair spaced at 90 degree intervals about the axis of socket. The lower face of the flange carries a ball formation of a ball and socket articulation. A second member in the form of ankle attachment plate has a concave seat that accepts the ball and threaded bores conforming to the through holes. The first and second members are held together by clamping screws received in the bores that fit onto washers having spherical lower faces that articulate on seats. The resulting alignment device is simple to manufacture and preserves angular position when an adjacent pair only of the clamping screws are removed. A similar alignment device having a cylindrical projection articulating in a cylindrical seat under the control of a single pair of clamping screws provides for heel height adjustment.

13 Claims, 14 Drawing Figures

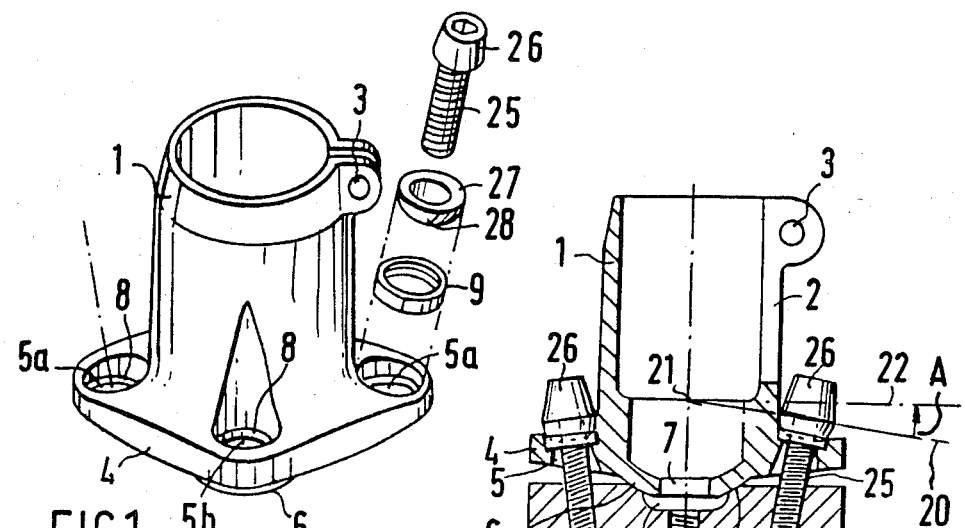
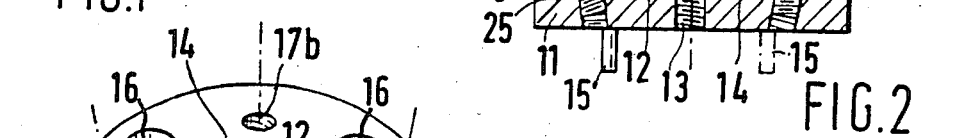
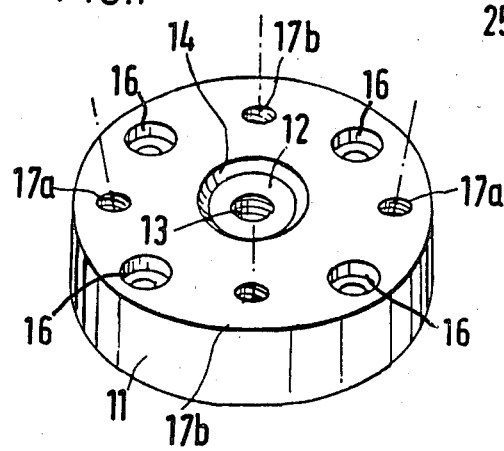
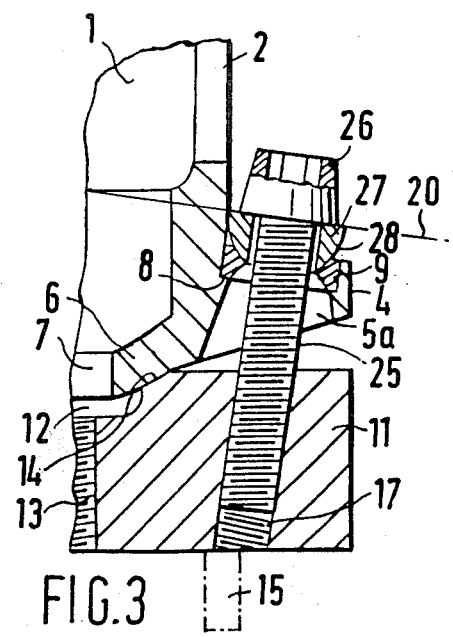
FIG.1 FIG.2 FIG.3

ALIGNMENT DEVICE FOR ARTIFICIAL LIMBS

FIELD OF THE INVENTION

This invention relates to an improved alignment device for artificial limbs of the kind intended to maintain a desired angular relationship between two structural elements. Such a device may be used, for example, for the adjustably aligned interconnection of a tube socket and supporting limb elements that may be the upper part of a prosthetic knee joint, a connector for a shin tube of a below-knee amputee, or an ankle connector for attaching a shin tube to an artificial foot.

BACKGROUND TO THE INVENTION

British Patent Specification No. GB-A-1494706 describes an alignment arrangement between a tube socket and an artificial limb element that comprised two oppositely facing concentric part-spherical convex surfaces provided on the end of the socket. The surfaces were engaged by complementary concave surfaces provided respectively within the limb element and within a clamping ring. Clamping screws passed through plain holes in the ring into threaded holes in the limb element, tightening thereof inducing a controlled degree of frictional resistance between the part-spherical surfaces. At least one pair of jacking screws passed through threaded holes in the ring on at least one diameter thereof to engage abutments on the socket. The arrangement enabled an angular alignment between the socket and the limb element set by operation of the jacking screws to be maintained by pure friction between the part-spherical surfaces. The above device has proven suitable for manufacture in light alloy and has also proven a success in service, but it is complex and it suffers from the problem that all the load passes through the clamping ring, which is relatively high stressed.

A further kind of alignment device for an artificial leg comprises a generally circular male member having a head formed with a multiplicity of recessed surfaces disposed at equi-angular intervals about the axis of the head and a body of larger diameter than the head and having a smoothly curved outer surface. A female member has a central bore into which the head of the male member fits and a multiplicity of screws in threaded bores in the female member disposed at equi-angular intervals and directed away from the entrance of the central bore. Accordingly, as the screws are tightened against the recessed surfaces the outer surface of the body is drawn into engagement with a complementary seat at the mouth of the bore. An arrangement of the above kind having four clamping screws is manufactured by Otto Bock in British Patent Specification No. 1307919 and one having three clamping screws is described in Patent Specification No. EP-A-0054391 (Robert Kellie & Son). Such an alignment device is of adequate strength when made in steel, but we have found that devices of this kind do not give adequate strength when made in light alloy, as is increasingly the practice in the prosthetic limb industry.

SUMMARY OF THE INVENTION

The problem with which this invention is concerned is the provision of an adjustable coupling that is inexpensive to manufacture and contains a minimum of different parts, that can be made in light alloy and achieve the required strength, and that is convenient for use by a limb fitter.

The present invention comprises an alignment device for a limb prosthesis comprising:

a first member having an end face, a convex surface protruding in a longitudinal direction from the middle of the end face, flange means extending transversely from the end of the first member, at least two apertures through the flange means at locations disposed symmetrically about the convex surface; means defining a concave or convex bearing surface on the face of the flange means that faces away from the convex surface on the end of the first member, each means overlying an aperture;

a second member having an end face formed with a concave seat that conforms to but is shallower than the convex surface of the first member so that the first member is supported with its flange means at a clearance from the second member whereby the first member can tilt on the second member, at least two threaded bores being formed in the second member at locations disposed symmetrically about the concave surface and conforming to the locations of the apertures, said bores converging at a small angle with increasing depth;

a member overlying each aperture having a hole therethrough, a generally planar top face and a convex or concave lower face tiltably received in the respective concave or convex bearing surface means; and at least two clamping screws passed through the holes in the tiltable members and the apertures in the flanges with their heads seating on the tiltable members and their threaded portions received in the bores of the second member, the first and second members being adjustable to a desired angular position when the screws are slack and being maintained at that angular position when the screws are tight.

DESCRIPTION OF PREFERRED FEATURES

In one embodiment the invention can be used as an alignment device for setting the attitude of upper and lower limb parts in both an anterior/posterior and in a medial/lateral plane. For that purpose three or preferably four clamping screws are provided, and the concave and convex surfaces above referred to are spherical so that the angular position of the first and second members can be adjusted in orthogonal directions. The bearing surfaces of the first member are concave and lie on a surface of revolution formed by rotating a line passing through the centre of curvature of the convex surface and directed towards the first member at a small angle from a normal to the axis of the convex surface about the axis of the convex surface, and the clamping screws fit with clearance the holes through the tiltable washers so that translational movements of the clamping screws relative to the first member within a small range consequent on tilting of the first member are taken up in the clearance between the tiltable members and the clamping screws. The first member may have a base flange that is generally rhombic in plan with four holes formed at the vertices of the rhombus, the longer diagonal of the rhombus lying in an anterior/posterior plane.

In a second embodiment the invention can be used between shin parts and keel of an artificial foot to provide heel height adjustment, the convex and concave surfaces being cylindrical with their axes in a medial/lateral plane. Only two clamping screws are then needed. An advantage of this version is preservation of a previously determined heel height if coupling has to be disassembled for other reasons such as repair to the limb. In the 2-screw version retaining one of the screws unaltered and removing the other preserves the heel height adjustment.

BRIEF DESCRIPTION OF DRAWINGS

Embodiments of the invention will now be described, by way of example only, with reference to the accompanying drawings, in which:

FIG. 1 is an exploded view of a first alignment device according to the invention;

FIG. 2 is a side section through the alignment device of FIG. 1;

FIG. 3 is an enlarged detail view of the base of a tube socket forming part of the alignment device of FIG. 1 in the vicinity of a clamping screw;

DETAILED DESCRIPTION OF PREFERRED EMBODIMENTS

Figure 4:
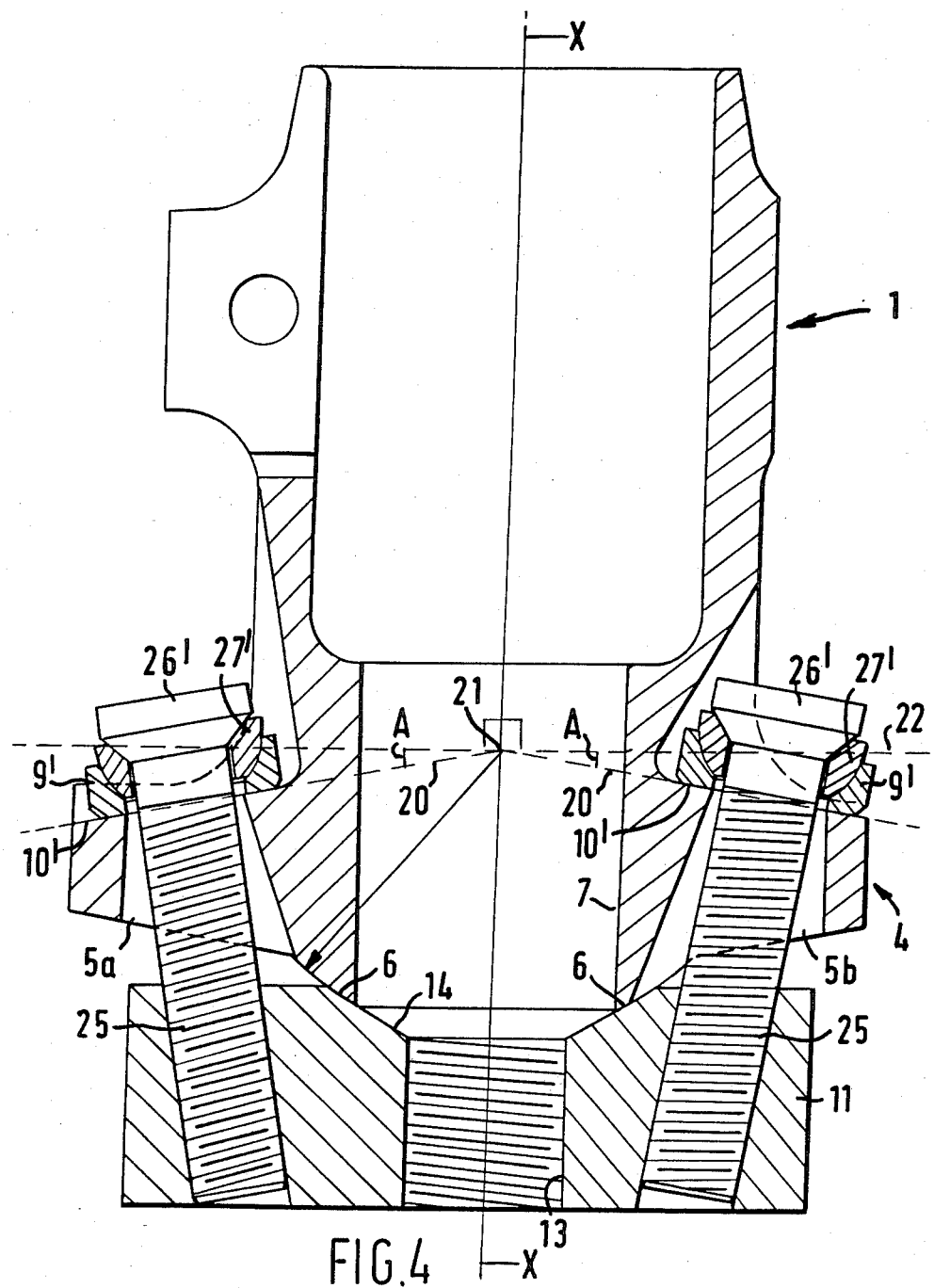
FIGS. 4 and 4a are repsectively a diagrammatic section of a second alignment device according to the invention and an underneath perspective view of a tube socket forming part of the alignment device of FIG. 4.

In FIGS. 1 to 3, there is shown a tube socket 1 having an axial slot 2 in its wall for reception and retention of a tubular artificial limb member (not shown) upon tightening a clamping screw (not shown) into a threaded hole 3. The socket 1 is machined from a solid piece of light alloy and is formed at its base with a flange 4 that is generally rhombic in plan and has adjacent its vertices four through-holes grouped into an anterior/posterior pair 5a and a medial/lateral pair 5b and spaced at 90 degrees around the axis of the socket 1. The upper and lower faces of the flange 4 are biconvex with a large radius of curvature, but the lower face has a part-spherical convex surface of lesser radius of curvature defining a ball formation 6 of a ball and socket articulation. A plain axial through-hole 7 through the centre of the ball 6 permits passage with clearance of a clamping bolt of a foot prosthesis. The holes 5 are stepped at 8 to accept annular seat inserts 9 presenting upwardly facing concave spherical seat surfaces. The seat surfaces are arranged to lie in a surface of revolution formed by rotating about the axis of the socket 1 a line 20 passing through the centre of curvature 21 of the ball 6 and directed downwardly at an angle A to a normal 22 to the axis of the socket. This geometrical condition is required for efficient articulation.

A limb element in the form in this instance of an ankle attachment plate 11 for a SACH foot has a recess 12 in its top face that is formed with a threaded hole 13 for passage of a foot clamping bolt and a spherical concave seat 14 that accepts the ball 6 of the tube socket. The lower face of the plate 11 carries locating pins 15 that engage the SACH foot for angular location thereof. Pairs of medial/lateral through holes 16 enable the plate 11 to be screwed or bolted to a SACH foot or other lower member. The plate 11 is also formed with threaded holes grouped in a medial/lateral pair 17b and an anterior/posterior pair 17a disposed about the seat 14 correspondingly to the holes 5a and 5b of the tube socket 1. The axis of each hole 17a, 17b is directed outwardly with respect to the axis of the seat 14 at the angle A which is a small angle, conveniently about 10 degrees.

The socket 1 is retained to the plate 11 by means of four clamping screws 25 that pass through the holes 5a, 5b and threadedly engage the holes 17a, 17b. The consequential outward tilt of the screws 25 means that their heads 26 are accessible to a screwdriver or key throughout the range of tilt of the socket 1 relative to the plate 11. The screws in the anterior/posterior holes 5a are further from the axis of the ball 6 and hence exert a greater turning moment for the same clamping force than the screws in the medial/lateral holes 5b. This reflects the forces in walking which are greater in the anterior/posterior plane than in the medial-lateral plane. A washer 27 having a convex spherical lower face 28 fits with clearance onto each of the screws 25 between the head 26 and the seat 9 on which it articulates. When the screws 25 are fitted, the rotational position between the socket 1 and the plate 11 is fixed. With the screws 25 slackened (most conveniently in transverse pairs) the angular position of the socket 1 relative to the plate 11 may be adjusted, with the washers 27 pivoting on the seats 9 and with the consequential small translational movement between the screws 26 and the socket 1 taken up by the clearance between the washers 27 and the screws 25. The screws may be repeatedly slackened and retightened to adjust the socket 1 to the required angular position and then finally tightened.

Figure 4A:
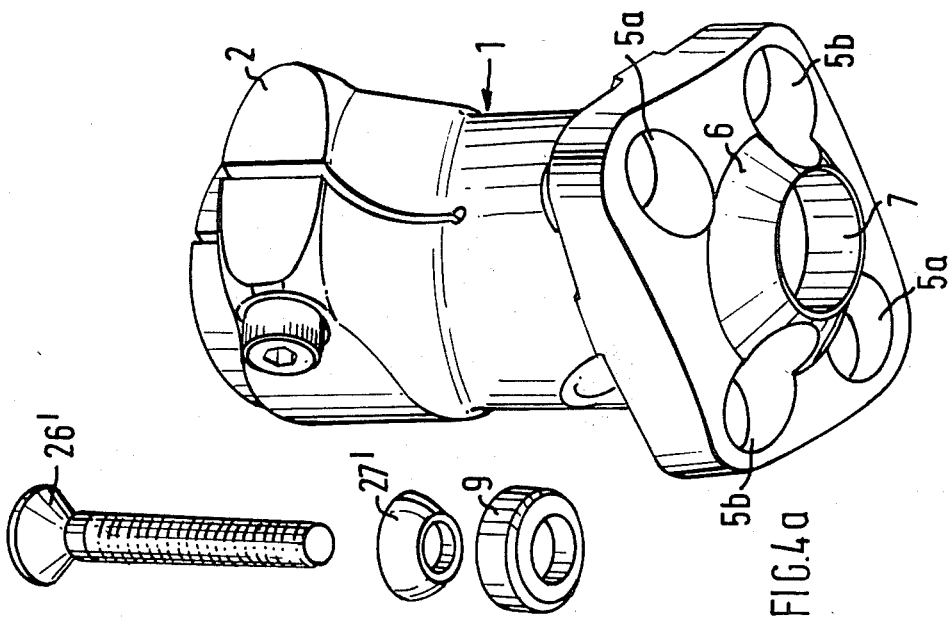

The arrangement in FIGS. 4 and 4a is generally similar except that the washers 9' are supported freely on planar inclined surfaces 10, 10' lying in planes passing through the ball centre of curvature 21, the angle A of surfaces 10, 10' being about 10°. The head of the screw 26' has a conical lower face that is received in a conical seat formed in the upper face of washer 27'. The arrangement in FIGS. 4 and 4a has the advantage that when the screws in one pair of holes 5a are being adjusted the consequential translational movement at the other pair of holes 5b is more readily accommodated. FIG. 4 is in two halves about its centre line, the left hand half showing the arrangement about a hole 5a and the right hand half showing that about a hole 5b.

Figure 5C:
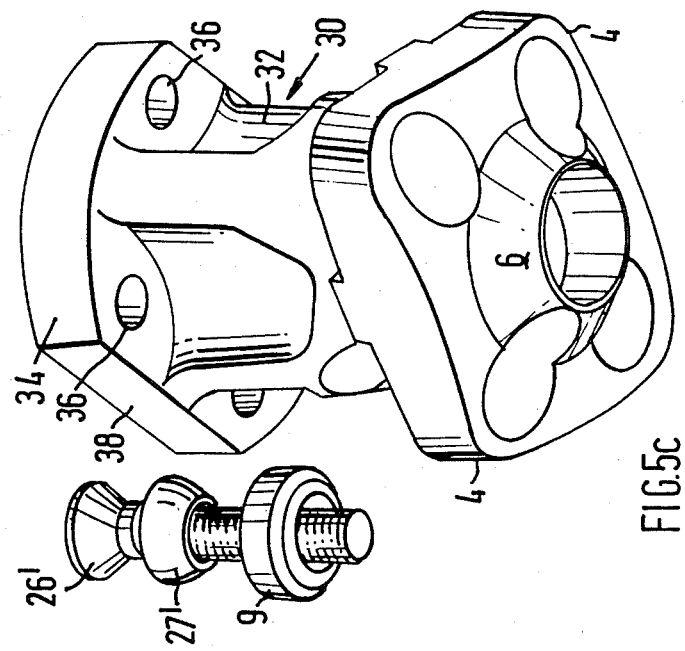
FIGS. 5a, 5b and 5c are respectively a plan, a side and an underneath perspective view of a platform alignment adaptor that may form part of an alignment device according to the invention.
Figure 5A:
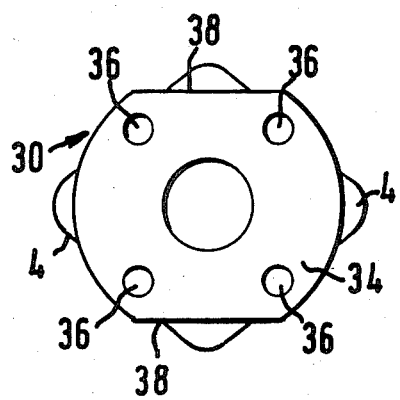
Figure 6A:
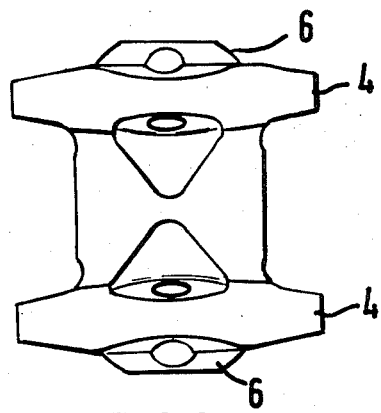
FIGS. 6a, 6b and 6c are respectively a side, sectional and plan view of a double ended alignment adaptor that may form part of an alignment device according to the invention.
Figure 6B:
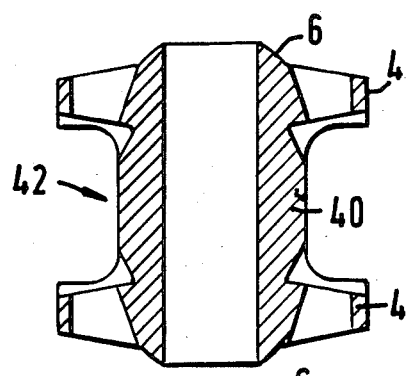
Figure 5B:
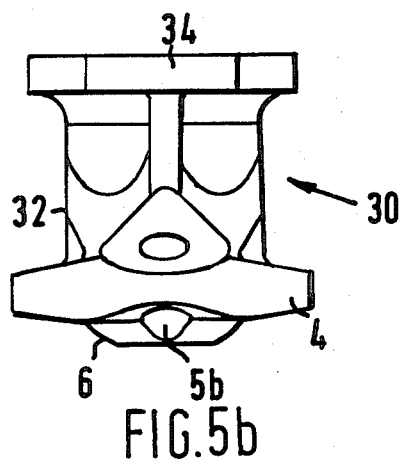
Figure 6C:
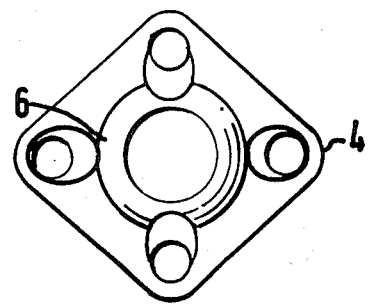

In FIGS. 1 to 3 and 4 and 4a the first member is in the form of a tube socket, but it will be understood that the alignment device may be used for other purposes. Thus FIGS. 5a to 5c show a platform alignment device 30 for connection between a stump socket and lower parts of the limb. The flange 4 and ball formation 6 occur at the lower end of a relatively short hollow stem 32 whose upper end is outwardly flanged to define a platform 34 provided with fixing holes 36 for upper parts of the limb. It will be noted that the generally rhomboidal arrangement of the flange 4 is preserved, the platform 34 being generally circular except for medial and lateral edges 38 defining notionally removed sectors. FIGS. 6, 6a and 6b show a further embodiment in which ball formations 6 occur at each end of a hollow stem 40 of a double-ended adaptor 42, thereby providing an alignment function independently at each end of the adaptor 42.

Figure 7:
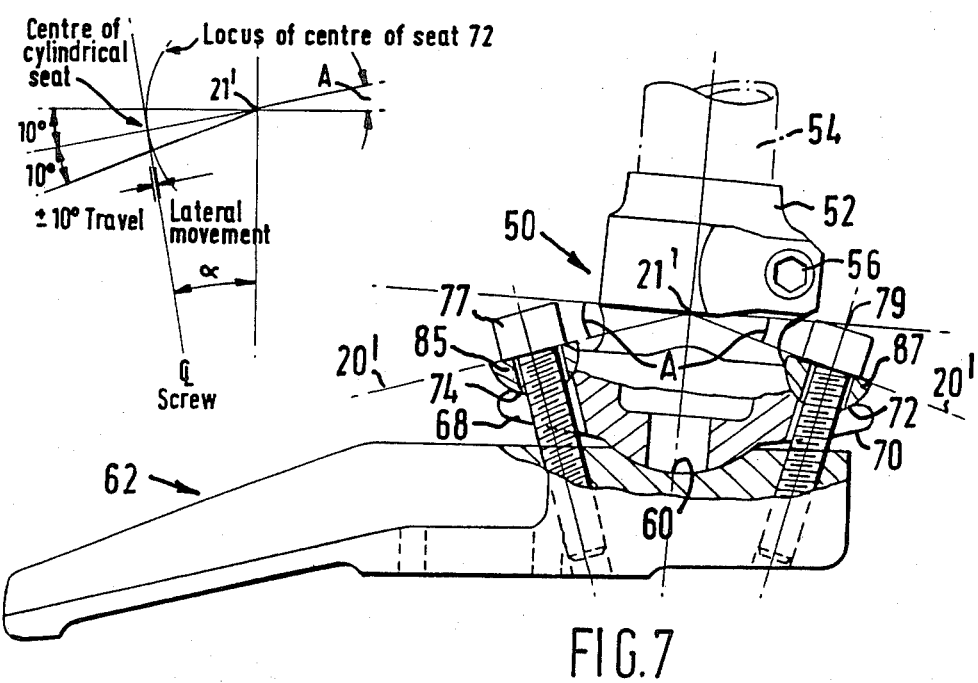
FIGS. 7, 8 and 9 are respectively a partly cut away side view, a plan view and an exploded view of a third embodiment of the invention that provides a coupling between a shin tube and a foot keel of an artificial foot with provision for adjustment of heel height.
Figure 8:
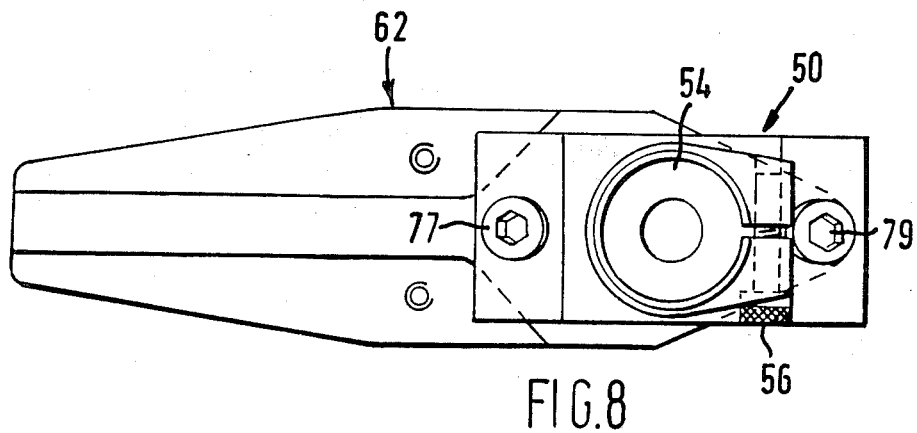
Figure 9:
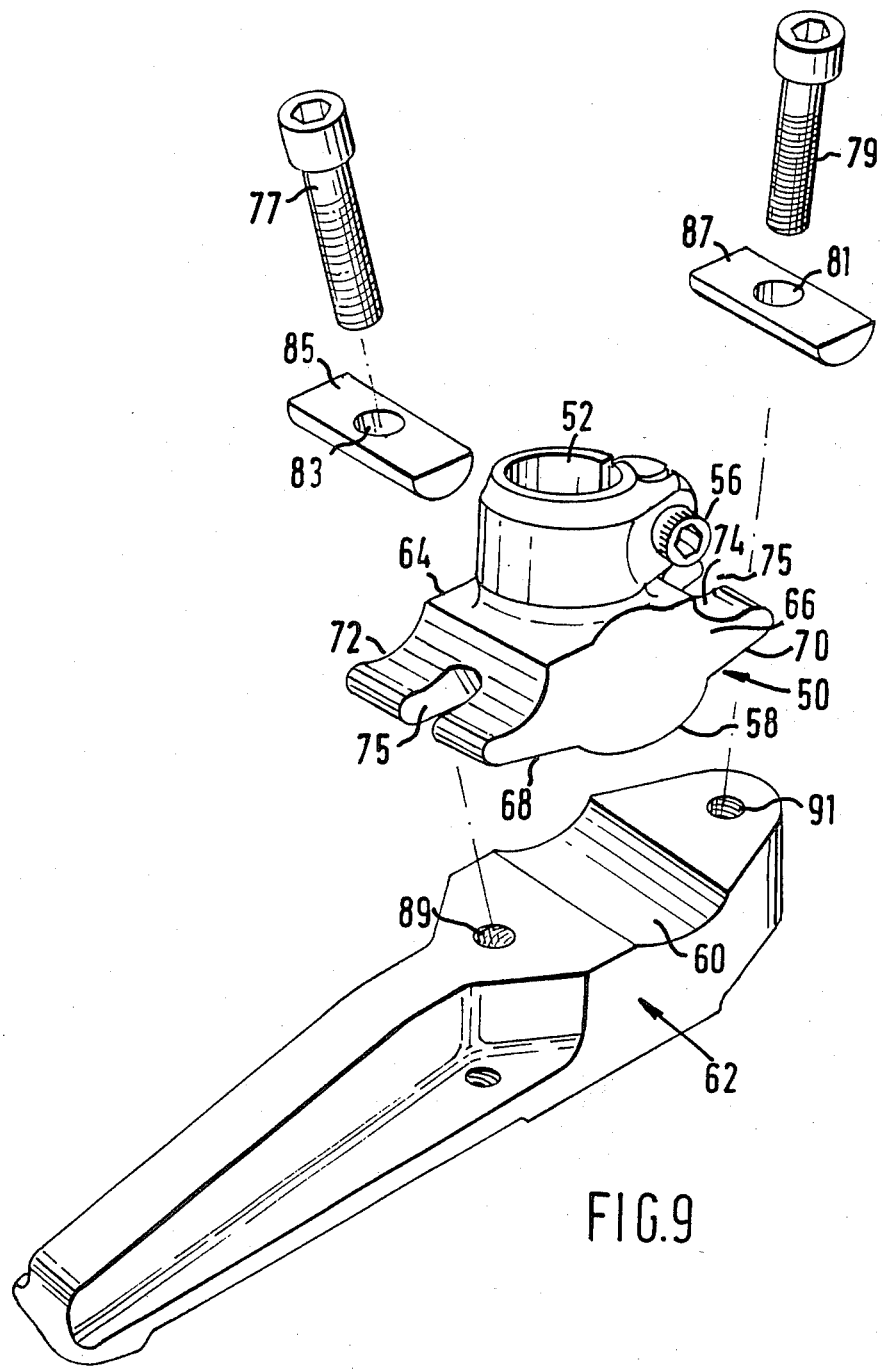

In FIGS. 7 to 9, there is shown a device for adjustment of the heel height of an artificial foot. An ankle connector generally indicated by the reference numeral 50 has a socket 52 for receiving the lower end of a shin tube 54 which is retained by a pinch bolt 56. The body of the connector 50 takes the form of a flange at the lower end of the socket 52 and its lower face has a part cylindrical convex surface 58 that seats in a corresponding part cylindrical seat 60 of a keel member generally indicated by reference numeral 62 of the artificial foot. Anterior and posterior portions 64, 66 have lower faces 68, 70 that slope upwardly as shown and have concave cylindrical seats 72, 74 in their upper faces. As will be seen the axes of surfaces 58, 60, 72, 74 are in medial-lateral direction to provide the required direction of pivoting. Slots 75 through the portions 72, 74 extend from the anterior and posterior edges of the connector 50 into the seats 72, 74 as shown. The connector 50 is held to the keel 62 by cap screws 77, 79 that pass through apertures 81, 83 in bars 85, 87 of D-profile whose curved lower faces rest on the seats 72, 74, the lower ends of the cap screws being received in threaded bores 89, 91 in the keep 62. With the screws 77, 79 slackened the angle of the keel 62 relative to the socket 52 may be set to achieve an intended heel height which is preserved when the screws are retightened.

As is apparent from FIG. 7, the bores 89, 91 are located and directed so that in the assembled coupling the interfaces between screws 77, 79 and bars 85, 87 are directed at right angles to the screws 77, 79 and pass through the centre of curvature 21' of the convex surface 58. Advantageously the positions and directions of the bores 89, 91 and of the centres of curvature of seats 72, 74 are positioned so as to minimise the effects of translational movements between the screws 77, 79 and the connector body 50 as the body 50 rocks relative to the keel 62 through its permitted range of angular travel. For this purpose, the radius of curvature of each seat 72, 74 lies slightly outside the centre line or axis of the screw 77, 79 when the body 50 is in the middle of its range of travel, so that the centre of curvature of each seat crosses from one side to the other of the centre line or axis of the screw and then back again as the full range of tilt of the member 50 is traversed. Lines 20' make equal angles A between a normal to the axis of the socket 54 and the interfaces between screws 77, 79 and bars 85, 87.

It will be appreciated that modifications may be made to the embodiments described above without departing from the invention, the scope of which is defined in the appended claims.

I claim:

1. An adjustable coupling for joining together parts of a limb prosthesis comprising:
    a first member having an end face, a convex surface protruding in a longitudinal direction from the middle of the end face, flange means extending transversely from the end of the first member, at least two apertures through the flange means at locations disposed symmetrically about the convex surface; means defining a concave or convex bearing surface on the face of the flange means that faces away from the convex surface on the end of the first member, each means overlying an aperture;
    a second member having an end face formed with a concave seat that conforms to but is shallower than the convex surface of the first member so that the first member is supported with its flange means at a clearance from the second member whereby the first member can tilt on the second member, at least two threaded bores being formed in the second member at locations disposed symmetrically about the concave surface and conforming to the locations of the apertures, said bores converging at a small angle with increasing depth;
    a member overlying each aperture having a hole therethrough, a generally planar top face and a convex or concave lower face tiltably received in the respective concave or convex bearing surface means; and
    at least two clamping screws passed through the holes in the tiltable members and the apertures in the flange means with their heads seating on the tiltable members and their theaded portions received in the bores of the second member, the first and second members being adjustable to a desired angular position when the screws are slack and being maintained at that angular position when the screws are tight.

2. A coupling according to claim 1, wherein the bores in the second member converge at about 20°.

3. A coupling according to claim 1, wherein the first and second members are of light alloy.

4. A coupling according to claim 1, wherein there are three or four clamping screws and said convex surface and seat are spherical so that the angular position of said first and second members can be adjusted in orthogonal directions.

5. A coupling according to claim 4, wherein the bearing surfaces of the first member are concave and lie in a surface of revolution formed by rotating about the axis of the convex surface a line passing through the centre of curvature of the convex surface and directed towards the first member at a small angle from a normal to the axis of the convex surface, and the clamping screws fit with clearance the holes through the tiltable washers so that translational movements of the clamping screws relative to the first member within a small range consequent on tilting of the first member are taken up in the clearance between the tiltable washers and the clamping screws.

6. A coupling according to claim 4 or 5, wherein the first member has a base flange that is generally rhombic in plan with four holes formed at the vertices of the rhombus, the longer diagonal of the rhombus lying in an anterior/posterior plane.

7. A coupling according to claim 6, wherein each hole is stepped to receive a seating washer of wear-resistant material presenting a part spherical bearing surface to the tiltable member.

8. A coupling according to claim 7, wherein the first member is a socket for a pylon tube.

9. A coupling according to claim 7, wherein the first member is a platform alignment adaptor.

10. A coupling according to claim 7, wherein the first member is a double-ended alignment adaptor.

11. A coupling as claimed in claim 1, wherein said convex and concave surfaces are cylndrical and the angular position of the first and second members is adjustable only in a single plane.

12. A coupling according to claim 11, wherein there are two clamping screws.

13. A coupling according to claim 11 or 12, wherein the first member is a socket for a pylon tube and the second member is a keel of a foot prosthesis.

* * * * *